(12) United States Patent
Tassakos et al.

(10) Patent No.: US 8,390,683 B2
(45) Date of Patent: Mar. 5, 2013

(54) METHOD AND DEVICE FOR THE QUALITY CONTROL OF A ROTATIONALLY SYMMETRICAL BODY, AND GRIP PERTAINING TO A HANDLING SYSTEM AND USED TO GRIP A ROTATIONALLY SYMMETRICAL BODY

(75) Inventors: Charalambos Tassakos, Stuttgart (DE); Leroklis Savvidis, Drama (GR)

(73) Assignee: INOS Automationssoftware GmbH (DE)

( * ) Notice: Subject to any disclaimer, the term of this patent is extended or adjusted under 35 U.S.C. 154(b) by 702 days.

(21) Appl. No.: 12/522,861

(22) PCT Filed: Jan. 11, 2008

(86) PCT No.: PCT/EP2008/000655
§ 371 (c)(1),
(2), (4) Date: Feb. 3, 2010

(87) PCT Pub. No.: WO2008/083995
PCT Pub. Date: Jul. 17, 2008

(65) Prior Publication Data
US 2010/0165096 A1    Jul. 1, 2010

(30) Foreign Application Priority Data
Jan. 12, 2007 (DE) .......................... 10 2007 002 624

(51) Int. Cl.
*H04N 7/18* (2006.01)
*G01N 21/90* (2006.01)

(52) U.S. Cl. ......................................... 348/92; 356/428
(58) Field of Classification Search ................... 348/92; 356/428
See application file for complete search history.

(56) References Cited

U.S. PATENT DOCUMENTS

| | | | |
|---|---|---|---|
| 3,811,567 A * | 5/1974 | Tomita et al. | 209/3.1 |
| 4,467,214 A | 8/1984 | Ito et al. | |
| 5,404,227 A * | 4/1995 | Sumita et al. | 356/428 |
| 6,186,873 B1 | 2/2001 | Becker et al. | |
| 6,523,330 B1 * | 2/2003 | Hurd | 53/405 |
| 2004/0183900 A1 * | 9/2004 | Karpen et al. | 348/92 |

* cited by examiner

*Primary Examiner* — Jay Patel
*Assistant Examiner* — Richard Torrente
(74) *Attorney, Agent, or Firm* — Donald R. Boys; Central Coast Patent Agency, Inc.

(57) ABSTRACT

The invention relates to a method and a device for the quality control of a rotationally symmetrical body (2, 2, 2") and a grip (4) of a handling system (5) for gripping a rotationally symmetrical body (2, 2, 2"). The aim of the invention is to improve the quality control of rotationally symmetrical bodies (2, 2, 2") in such a way that it is faster, reliable and more economical. To this end, the grip (4) comprises grip fingers (26) having rotationally symmetrically holding elements (29, 31) for holding the body (2, 2, 2"), the holding elements (31) being mounted in the grip fingers (26) in such a way that they can be rotated about the rotational axes (29) thereof. In order to grip the body (2, 2, 2"), the grip fingers (26) are displaced on a circular path. A central drive mechanism (22; 35) is respectively provided for the rotational movement of the holding elements (29, 31) of all of the grip fingers and for the rotational movement of all of the grip fingers (26).

10 Claims, 6 Drawing Sheets

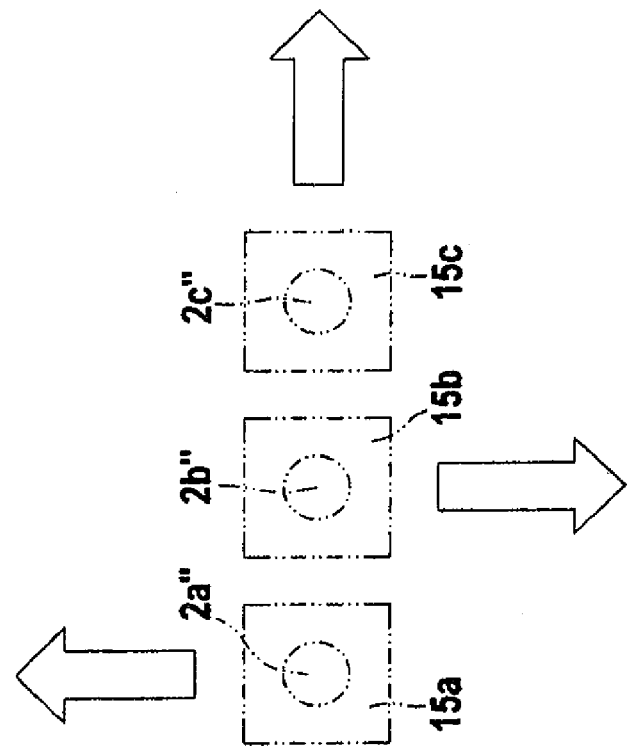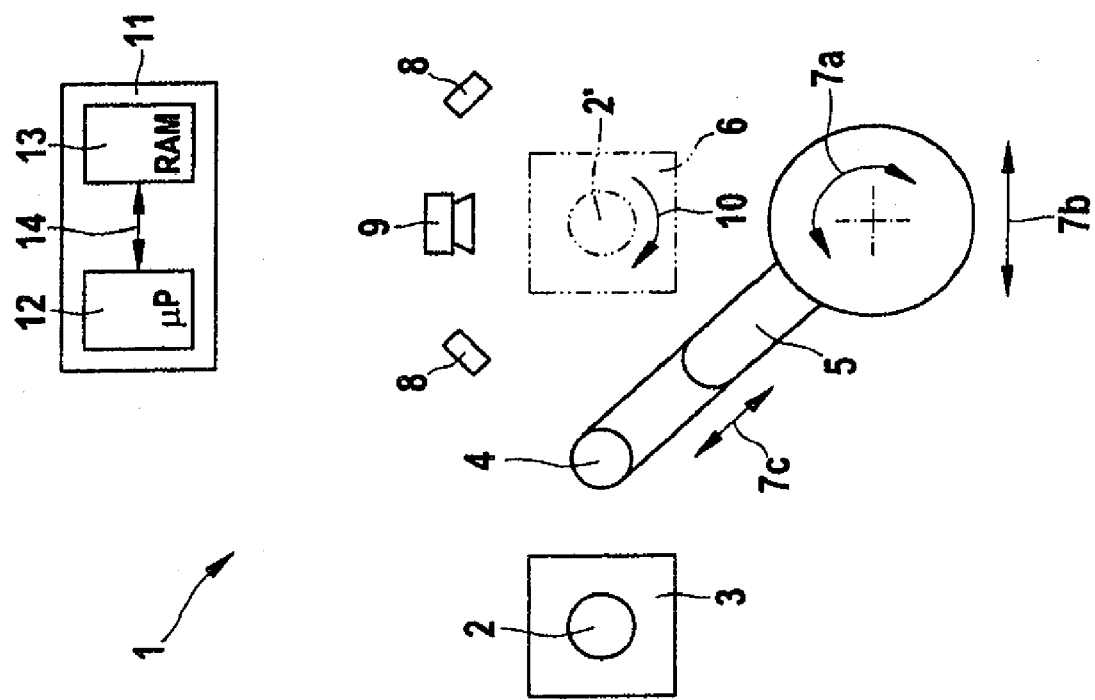
Fig. 1

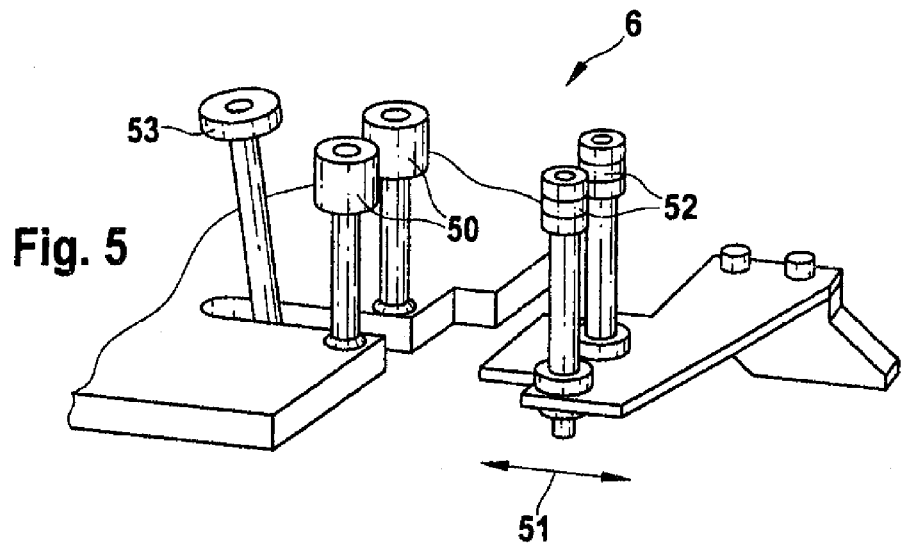
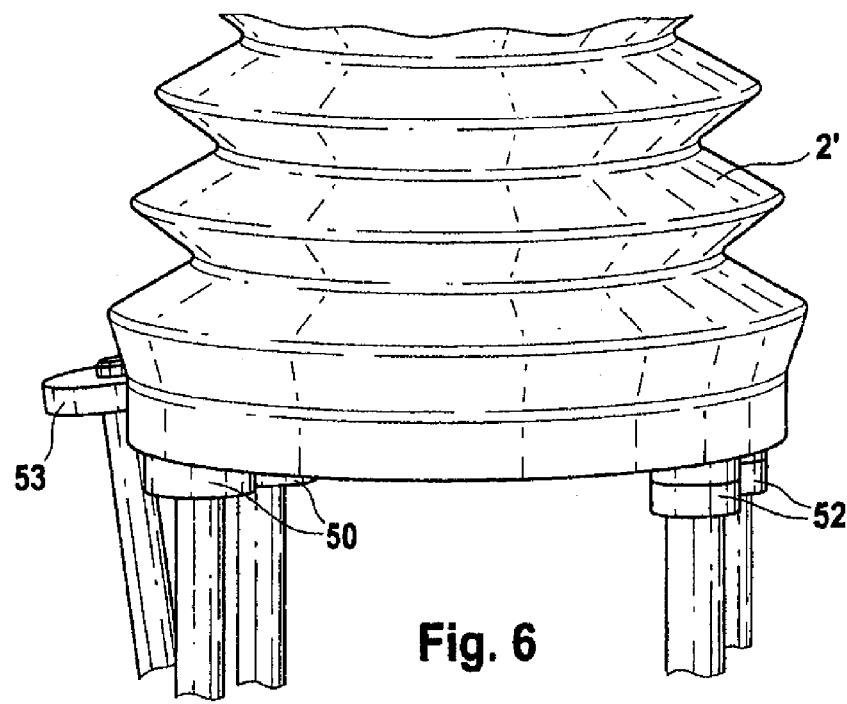

METHOD AND DEVICE FOR THE QUALITY CONTROL OF A ROTATIONALLY SYMMETRICAL BODY, AND GRIP PERTAINING TO A HANDLING SYSTEM AND USED TO GRIP A ROTATIONALLY SYMMETRICAL BODY

CROSS-REFERENCE TO RELATED DOCUMENTS

The present application claims priority to German patent application serial number 10 2007 002 624.4, which was filed on Jan. 12, 2007, which is incorporated herein in its entirety, at least by reference.

The present invention relates to a method for quality control of a rotationally symmetrical body. The body is gripped by a gripper of a handling system, transported to a working position and optically scanned there. The invention also relates to an apparatus for quality control of a rotationally symmetrical body. The apparatus has a handling system with a gripper for gripping the body and for transportation of the body to a working position as well as at least one electronic camera for optical scanning of the body in the working position. Finally, the present invention relates to a gripper of a handling system for gripping a rotationally symmetrical body.

One example of rotationally symmetrical bodies for the purposes of the present invention is an axle boot in order to cover the attachment of a motor vehicle axle boot. However, the invention is applicable to rotationally symmetrical bodies of any type. Axle boots essentially have a hollow-conical shape with a casing in the form of bellows. Axle boots are filled with lubricant, in particular grease, during operation of the motor vehicle. They must remain sealed throughout the entire life of the motor vehicle since, otherwise, this can lead to loss of lubricant and therefore an adverse effect on the operation of the axle boot, and even to the axle boot becoming defective.

In order to produce axle boots, heated plastic material is pressed into a mold using compressed air, and material residues are cut off at the top and bottom after the material has cooled down. During this process, the material may be weakened at points, that is to say the material is thinner than intended in places, and cuts may even occur in the boot itself. These and other defects in the finished axle boot must be identified during quality control.

Manual quality control of rotationally symmetrical bodies following manufacture is known from the prior art. Using the example of axle boots, these boots are picked up manually by appropriately trained and instructed people and are checked visually for quality defects. However, this has the disadvantage that the defects are not all always reliably identified. Furthermore, manual quality control is relatively slow and, because of the time fluctuations in the control process, it is virtually impossible to integrate into an automated manufacturing process and, furthermore, it is relatively expensive.

Admittedly, and purely theoretically, certain steps in manual quality control could be automated (for example the gripping of the bodies or the optical scanning of the bodies), although this has not been possible until now, because of the lack of availability of suitable grippers.

Other examples of rotationally symmetrical bodies are yoghurt cartons or other rotationally symmetrical vessels, containers or covers composed of plastic.

Against the background of this prior art, the present invention is based on the object of carrying out quality control of rotationally symmetrical bodies more quickly, more reliably and more cost-effectively.

Against the background of the method of the type mentioned initially, this object is achieved in that the body is rotated at least at times about its rotation axis by the gripper in the working position.

The method according to the invention therefore makes use of a gripper which can rotate, at least at times, the gripped rotationally symmetrical body in the working position, that is to say during the optical scanning. This allows the use of static electronic cameras for recording images of the external and/or internal circumferential surface of the body. The gripper preferably rotates the body at a constant rotation speed, thus simplifying and speeding up the processing and evaluation of the recorded images. The cameras are preferably CMOS and/or CCD cameras. The cameras may be in the form of slot cameras, which record an image with a width of only one pixel or an image of the body which is considerably narrower than its height. Slot cameras have the advantage that they can record a wide area of the body in height, preferably the entire height, and despite good resolution they provide images with a relatively small number of pixels (owing to the narrow width of the images), which can be processed and evaluated quickly.

In theory, a single camera positioned in a suitable manner is sufficient to record the circumferential area of interest of the body. The body rotates in front of the camera, as a result of which this camera can record the surface area of interest over the entire circumference of the body. However, in practice, particularly in the case of relatively complex bodies, for example having a circumferential surface in the form of bellows, a plurality of cameras are used in order to allow the surface of the body to be recorded completely, for example the folds of the bellows from both sides. It is also feasible to provide separate cameras for recording of the inside and of the outside of the body, for rotationally symmetrical hollow bodies.

The images recorded by the cameras are processed and evaluated by suitable image processing software. The evaluation algorithms that are used in this case depend on the quality defects to be detected.

The method according to the invention is particularly suitable for quality control of rotationally symmetrical bodies, preferably hollow bodies, such as bellows, vessels, containers or covers. These may be manufactured from any desired materials, may be rigid (for example stone, wood, metal, plastic) or flexible and resilient (for example plastic, rubber, foam). The invention will be explained in more detail with reference to a hollow-cylindrical axle boot having a casing which is in the form of bellows and is composed of plastic, but is expressly not restricted to this.

For quality control of flexibly deformable hollow bodies, it is advantageous for the body to be forcibly deformed at least at times throughout the duration of the scanning. The body is preferably strained at least at points or in places in the area of its external circumferential surface during the deformation. For this purpose, it is feasible for the body to be forcibly guided by rollers or guide rails during the rotation process, at its end that is opposite the end that is gripped by the gripper. The forced guidance changes the body to a shape which differs from its original or rest shape. In this case, specific quality defects, for example cracks or cuts, can be seen better, for example because they split open.

Alternatively or additionally, it is proposed that the body be strained at least at points or in places in the area of its internal circumferential surface during the deformation.

After the optical scanning, the body is preferably transported by the handling system from the working position to one specific one of a plurality of available intermediate storage positions depending on the result of the quality control. This allows the bodies that have been checked to be sorted into sound and defective bodies. Furthermore, the defective bodies can be sorted on the basis of type, number and extent of the defects, and on the basis of further criteria. The intermediate storage position may be a holding position on a conveyor belt or a slide for transportation of the bodies away, a stack position for stacking a plurality of bodies one on top of the other, or simply an opening in a holding container.

The object on which the present invention is based is also achieved by an apparatus of the type mentioned initially, which is characterized in that the gripper of the handling system has gripping fingers with rotationally symmetrical holding elements for firmly holding the body, with the holding elements being designed such that they can rotate about their rotation axes. The rotation axes of the holding elements preferably run parallel to one another. The handling system preferably positions the gripper with respect to the body such that the gripper can grip the body such that the rotation axis of the body runs essentially parallel to the rotation axes of the holding elements. Minor discrepancies between the rotation axes relative to one another can be compensated for during the course of recording of the images by the cameras and/or the processing and evaluation of the recorded images.

The apparatus preferably comprises an open-loop and/or closed-loop control unit, which controls the gripper, the camera or cameras and the image processing software such that the apparatus carries out the method according to the invention.

The object on which the present invention is based is also achieved by a gripper of the type mentioned initially, which is characterized in that the gripper has gripping fingers with rotationally symmetrical holding elements for firmly holding the body, with the holding elements being mounted in the gripper such that they can rotate about their rotation axes. The gripper according to the invention is designed in a particularly advantageous manner such that the gripped body can be rotated in the field of view of the camera, which is arranged in a static position, in the working position, without movement of the handling system and without any position change or rotary movement of the gripper.

The rotation axes of the holding elements preferably run parallel to one another and/or at right angles to the movement direction of the gripping fingers for gripping the body. This allows a particularly simple, robust and cost-effective implementation of the gripper.

It is particularly advantageous if the movement direction of the gripping fingers for gripping the body runs on a circular path. This ensures secure and reliable gripping of the body and, to a limited extent, a self-centering function of the body relative to the gripper during the access by the gripper, without a displaced body being tilted or knocked over by the access of the gripper.

In order to achieve the rotational movement of the holding elements of the gripper, it is proposed that the holding elements are each connected in a rotationally fixed manner to a gearwheel, with the gearwheels of all the gripping fingers engaging indirectly with a central gearwheel of the gripper. The gearwheels are each connected indirectly via at least one further gearwheel to the central gearwheel. The gripper has a first drive mechanism which causes the central gearwheel to carry out a rotational movement. All the gearwheels are mounted on a common part of the gripper, such that they can rotate. The first drive mechanism preferably has an electrical drive. In addition, it has a transmission unit, which converts the rotary movement of the electric motor to a rotational movement of the shafts.

In order to provide the gripping movement of the gripping fingers on a circular path, it is proposed that the gripping fingers are connected in a rotationally fixed manner to a respective shaft, with the shafts running through the further gearwheels of the gripping fingers such that they can rotate, and with the gripper having a second drive mechanism which causes the shafts to carry out a rotary movement. This refinement of the gripper allows rotation of the holding elements and therefore of the gripped body independently of the gripping movement of the gripping fingers. The rotation axes of the shafts advantageously run parallel to the rotation axes of the gearwheels. The second drive mechanism preferably has a pneumatic drive. The pneumatic drive allows accurate, sensitive, proportional movement of the gripping fingers. The gripping forces with which the gripping fingers grip the body can be varied or adjusted, for example depending on the robustness of the gripped body or of the body to be gripped.

One preferred exemplary embodiment of the invention will be explained in more detail in the following text with reference to the drawings, in which:

FIG. 1 shows a schematic view from above of an apparatus according to the invention for quality control of rotationally symmetrical bodies according to one preferred embodiment;

FIG. 5 shows means for holding and forced deformation of the body in the working position;

FIG. 6 shows the means shown in FIG. 5 with a body held therein; and

Figure 2:
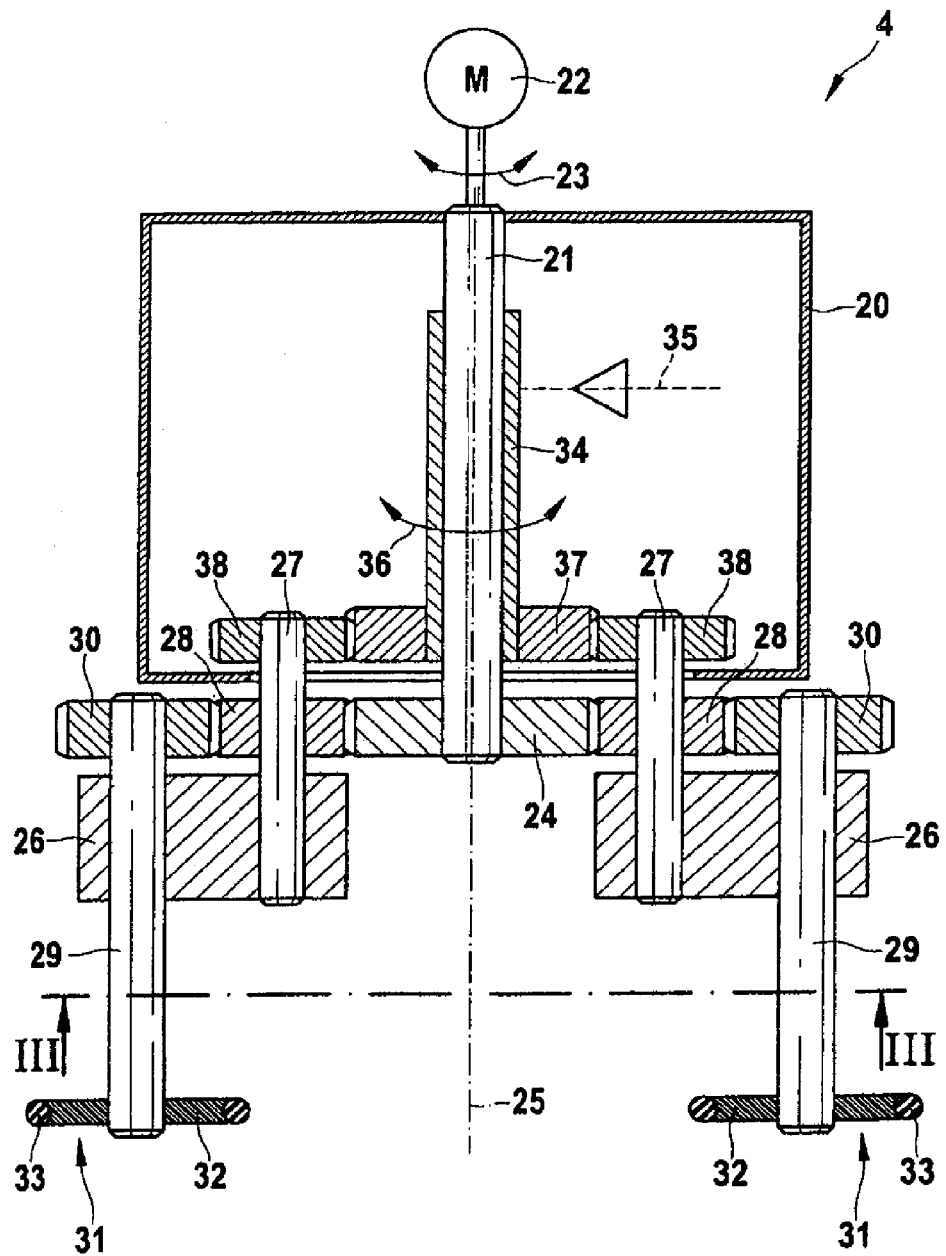
FIG. 2 shows a side view, in the form of a section, of a gripper according to the invention of an apparatus as shown in FIG. 1.

In FIG. 1, an apparatus according to the invention for quality control of rotationally symmetrical bodies is annotated in its totality with the reference sign 1. In the exemplary embodiment, a hollow body composed of a flexible material is used as the rotationally symmetrical body, in particle an axle boot or drive shaft boot composed of plastic or rubber in order to provide a flexible cover for joints on a drive shaft in a motor vehicle. An axle boot has an essentially hollow-cylindrical shape and has a cylinder casing in the form of a bellows. The body is illustrated only schematically in FIG. 1, and is annotated with the reference sign 2.

Starting from a feed position 3, the bodies 2 are gripped individually by a gripper 4 of a handling system 5, and are transported to a working position 6. The body in the working position 6 is annotated with the reference sign 2'. By way of example, the handling system 5 is an industrial robot with a multiple-joint gripping arm at whose end the gripper 4 is arranged. The handling system 5 or the gripping arm of the system 5 can be moved in a plurality of directions, some of which are illustrated by way of example in FIG. 1, and are annotated with the reference signs 7a, 7b, 7c. Instead of a multiple-joint robot arm, a handling system 5 with linear movement axes, preferably with two linear movement axes, can also be used. In the working position 6, means are provided for optical scanning of the surface of the body 2'. The means comprise at least one lighting device 8, for example a gas-discharge lamp or a plurality of semiconductor light sources which can emit light at any desired wavelength in the visible or invisible (UV-, IR-) range, as well as at least one electronic camera 9, for example a CCD camera or a CMOS camera which records images of the outer surface of the body 2'. The camera 9 is preferably in the form of a slot camera, which records an image of the body 2' with the width of a few pixels, preferably of only one pixel, and with a height of several tens of pixels, normally several hundred, and in some circumstances even several thousands of pixels. A greater or lesser number than the number of lighting devices 8 shown in FIG. 1 and the illustrated camera 9 may, of course, also be used. In particular, it is feasible to use separate lighting devices 8 and cameras 9 in order to record the outer surface and the inner surface of the body 2'.

One important aspect of the present invention is that the body 2' is rotated in the working position 6 such that the camera 9 can record a plurality of images of the body 2', and can in this way record the entire circumferential surface of the body 2', despite the restricted recording area, during the rotation of the body 2'. The rotation 10 of the body 2' is achieved by means of a gripper 4, which is designed in a particular manner and has rotationally symmetrical holding elements which are caused to carry out a rotational movement by a drive mechanism. The configuration of the gripper 4 will be explained in detail further below. The rotation 10 of the body 2' can be carried out in any desired direction, and preferably at a constant speed.

The images recorded by the camera or cameras 9 are transmitted to an open-loop and closed-loop control device 11, where they are processed and evaluated in order to detect quality defects in the body 2'. Quality defects to be detected include, for example, cuts, cracks in the material or weakening of the material of the body 2'. The images may be transmitted to the open-loop and closed-loop control device 11 in any desired manner, in particular by cables, IR or radio.

The open-loop and closed-loop control device 11 has at least one computation appliance 12, for example in the form of a microprocessor or a programmable logic controller (PLC) and memory means 13, for example in the form of a ROM or RAM, in which software is stored for open-loop and closed-loop control of the method according to the invention. In order to run the software, this software is transmitted via a data transmission link 14, for example in the form of an internal data bus, from the memory element 13 to the computation appliance 12. Variables which are calculated or read while the software is being run are likewise transmitted from the computation appliance 12 via the link 14 to the memory element 13, and can be stored there. In order to achieve open-loop and/or closed-loop control of the procedure for the method according to the invention, the device 11 is connected to the handling appliance 5, to the gripper 4, to the lighting means 8 and to the camera 9. The connection can be provided by cable or in a wire-free manner (for example radio or IR).

Finally, image processing software can also be stored in the memory element 13, in order to process and evaluate the images received from the camera or cameras 9, for detection of quality defects in the body 2'. The handling appliance 5 and the gripper 4 are operated as a function of the result of the evaluation of the images, in order to transport the body 2' from the working position 6 to one of a plurality of available intermediate storage positions 15a, 15b, 15c, and to place it down there. The bodies in the intermediate storage positions are annotated 2a", 2b" and 2c". This allows the bodies 2' that have been checked to be sorted into sound and defective bodies 2". Furthermore, it is possible to sort the defective bodies 2" on the basis of the nature, number and extent of the defects, and on the basis of further criteria. Bodies 2a" which have been placed down in the intermediate storage position 15a are ejected from the apparatus 1. Bodies 2' are placed at the position 15a in response to a command from a user of the apparatus, allowing manual checking of the fully-automatically checked body 2'. Defective bodies 2b" are placed down in the intermediate storage position 15b. These can be collected in a catchment container, into which they are passed either directly or indirectly via a conveyor belt, a slide or the like. Sound bodies 2b" are placed in the intermediate storage position 15c. These can be collected in a catchment container, to which they are passed, either directly or indirectly via a conveyor belt, a slide or the like. The bodies 2b" and/or 2c" can also be stacked in the intermediate storage position 15b, 15c.

FIG. 2 shows one preferred embodiment of the gripper 4 according to the invention in detail. The gripper 4 comprises a hollow-cylindrical housing 20 via which the gripper 4 is attached to the distal end of the gripping arm of the handling appliance 5. A central shaft 21 is mounted in the housing 20 such that it can rotate, and be caused to carry out a rotational movement 23 by an electric motor 22. The longitudinal center axis 25 of the housing 20 is preferably coincident with the longitudinal axis of the central shaft 21. The rotational movement 23 is controlled by the open-loop and closed-loop control device 11. The electric motor 22 is connected to the shaft 21 via a suitable transmission (not illustrated). Contrary to the illustration shown in FIG. 2, the electric motor 22 can also be arranged within the housing 20. A central gearwheel 24 is attached in a rotationally fixed manner to the lower end of the shaft 21.

Three gripping fingers 26 are arranged at angular intervals of 120° from one another on the lower face of the housing 20. More or less than the three gripping fingers 26 described in this exemplary embodiment, may, of course, also be provided. The gripping fingers 26 are each attached to a gripper shaft 27 in a rotationally fixed manner, and this gripper shaft 27 is mounted in the housing 20 such that it can rotate. Further gearwheels 28 are mounted on the shaft 27 such that they can rotate, and all engage with the central gearwheel 24. The shafts 27 therefore form the rotation axes for the further gearwheels 28. Finally, a respective holding element shaft 29 is mounted in the gripping fingers 26 such that it can rotate, to one end of which holding element shaft 29 a gearwheel 30 is attached, which engages with the corresponding further gearwheel 28, while a holding element 31 is attached to its other end in a rotationally fixed manner. The holding elements 31 are rotationally symmetrical and each comprise an element 32 which is in the form of a plate, is composed of a rigid material (for example a plastic) and is surrounded by an annular element 33 composed of a material with a high coefficient of friction (for example a plastic or rubber), and possibly a ground surface.

Operation of the electric motor 22 therefore causes the holding element 31 to carry out a rotational movement via the shafts 21 and 29 and via the gearwheels 24, 28 and 30. A body 2 that has been gripped can therefore be rotated in the working position 6 in the recording area of the camera or cameras 9, in such a way that the entire circumference of the body 2' can be recorded by a small number of stationary cameras 9.

A sleeve 34 is mounted on the central shaft 21 such that it can rotate, and can be caused to carry out a rotary movement 36 by means of a pneumatic drive mechanism 35. The rotary movement 36 is controlled by the open-loop and closed-loop control device 11. The pneumatic drive 35 is connected to the sleeve 34 via a suitable transmission (not illustrated). Contrary to the illustration shown in FIG. 2, the pneumatic drive 35 can also be arranged outside the housing 20. A further central gearwheel 37 is attached in a rotationally fixed manner to the lower end of the sleeve 34.

Gearwheels 38 are mounted in a rotationally fixed manner on the gripper shafts 27 and engage with the central gearwheel 37. Operation of the pneumatic drive 35 therefore causes the gripping fingers 26 to carry out a circular rotary movement about the longitudinal axes of the shafts 27, via the sleeve 34, the shaft 27 and via the gearwheels 37 and 38. The movement to open and close the gripper 4 and to grip and release a body 2 is therefore carried out in the case of the gripper 4 according to the invention non-linearly, but on a circular path. This refinement of the gripper 4 allows a combination of rotation of the holding elements 31 and a gripping movement of the gripping fingers 26 using a gripper 4 of particularly simple and robust design.

It is, of course, feasible for the rotary movement of the gripping fingers 26 and the rotational movement of the holding elements 31 to be carried out by means of drive mechanisms 22, 35 other than those mentioned. In particular it is also possible to use a hydraulic drive or—at least for the gripping movement of the gripping fingers 26—an electromagnetic drive. Furthermore, the number, configuration, arrangement and mounting of the gearwheels 24, 28, 30, 37, 38 may differ from the described exemplary embodiment. In particular, it is feasible not to use any gearwheels to create the rotary movement of the gripping fingers 26 and/or the rotational movement of the holding elements 31. Instead of this, for example, it is possible to use a belt drive or some other drive for each gripping finger 26 or for each holding element 31.

Figure 3:
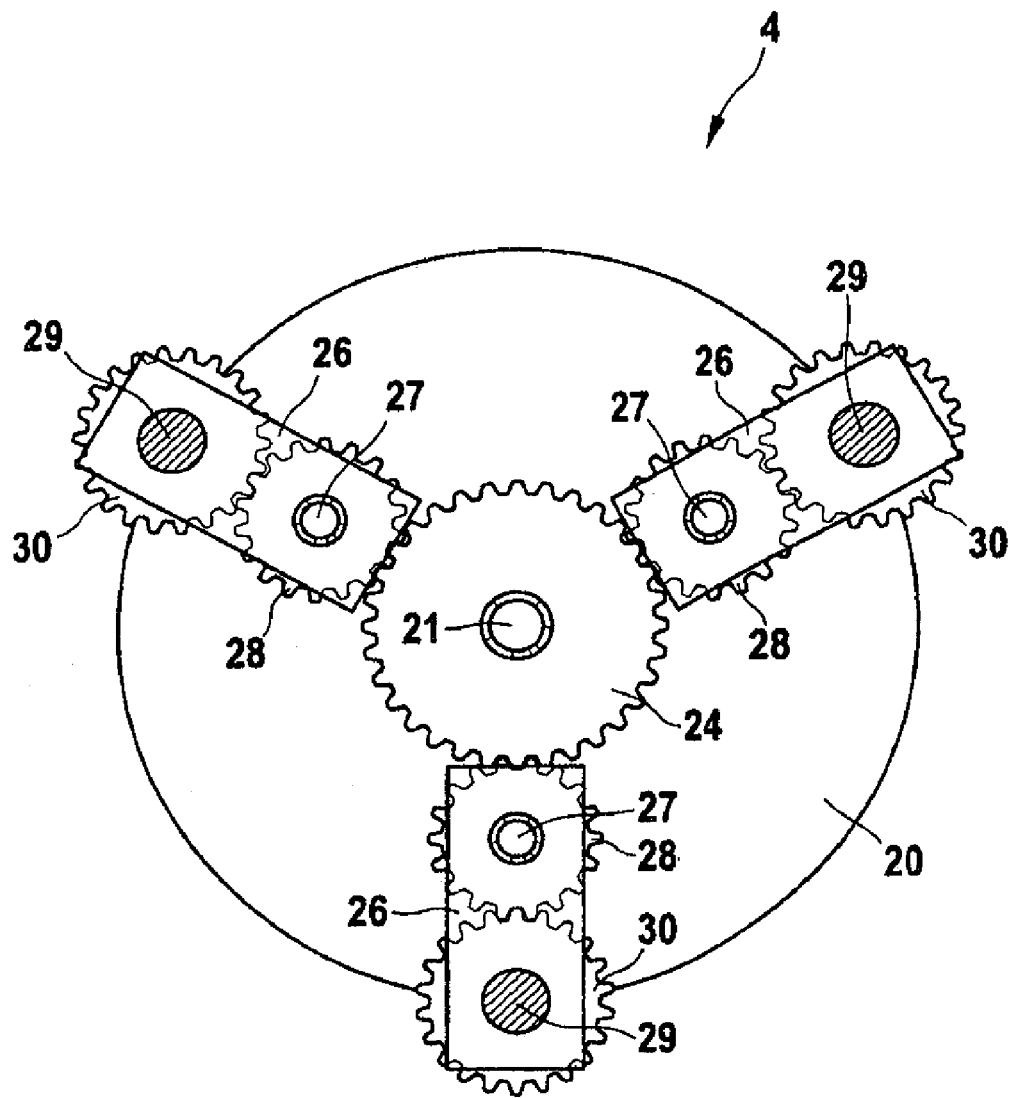
FIG. 3 shows a view of the gripper from underneath along the line III-III in FIG. 2.

In order to illustrate it better, FIG. 3 once again shows the gripper 4 according to the invention, from underneath, along the line III-III from FIG. 2. Identical components have been annotated with identical reference signs.

Figure 4:
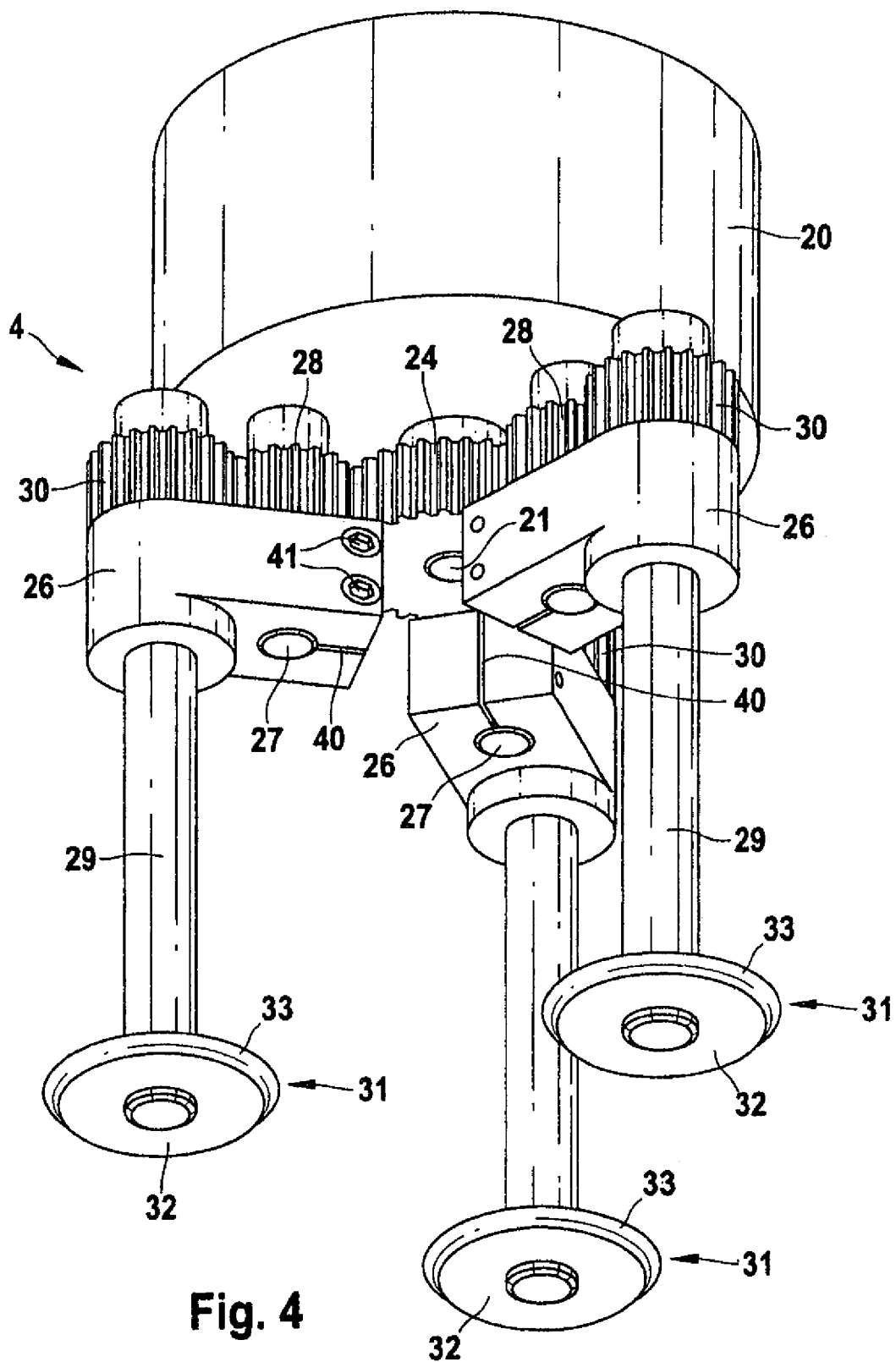
FIG. 4 shows a perspective view of the gripper shown in FIG. 2.

FIG. 4 shows a perspective view of the gripper 4 according to the invention. In this case as well, identical components have been annotated using identical reference signs. FIG. 4 clearly shows that the gripping fingers 26 each have an opening with a slot 40. In order to fit the gripper 4, the shaft 27 is inserted into the opening. Screws 41, which are provided in the area of the slot 40 in the gripping finger 26, are then screwed tight. The gripping finger 26 is thus drawn together in the area of the slot 40 and the opening, as a result of which the shaft 27 is mounted in the opening in a rotationally fixed manner.

FIG. 5 shows the working position 6 in detail. This working position 6 comprises two rollers 50, which are arranged such that they are stationary and are mounted such that they can rotate, as well as three rollers 52 and 53, which can move linearly in the direction of an arrow 51 and are likewise mounted such that they can rotate. The rollers 52 and 53 are preferably connected to one another and are preferably moved jointly. The rollers 52 and 53 may be moved hydraulically, pneumatically, by electric motor, electromagnetically or in some other manner. The linear movement 51 of the rollers 52 and 53 is preferably controlled by the open-loop and closed-loop control device 11. The rotary movement of the rollers 50, 52 and 53 is preferably passive, that is to say without any active drive.

In the initial position, the rollers 52 and 53 have been moved to the left. The rotationally symmetrical hollow body 2' is arranged in the working position 6 such that the casing of the body 2' is located between the rollers 50 and the roller 53 on one side and outside the rollers 52, that is to say to the right of the rollers 52, on the other side (cf. FIG. 6). The rollers 52 and 53 are then moved to the right (cf. FIG. 7). The hollow body 2' is therefore held in a specific position by the rollers 50 and 52 arranged therein. The circular grooves which are formed on the circumference of the rollers 52 make it harder for the casing of the body 2' to slide off the rollers 52. Furthermore, the roller 53, which has been moved to the right, presses the casing of the hollow body 2' into the space between the rollers 50. The casing is therefore deformed in the area of the roller 53 or of the space between the rollers 50. The body 2' is deformed at times over its entire circumference by rotation of the body 2' about its rotation axis. This allows simpler, more reliable and quicker detection of specific quality defects in the body 2. In particular, slits and cracks are split open in this way, that is to say they have a greater width and can therefore be seen more easily and more reliably.

Figure 7:
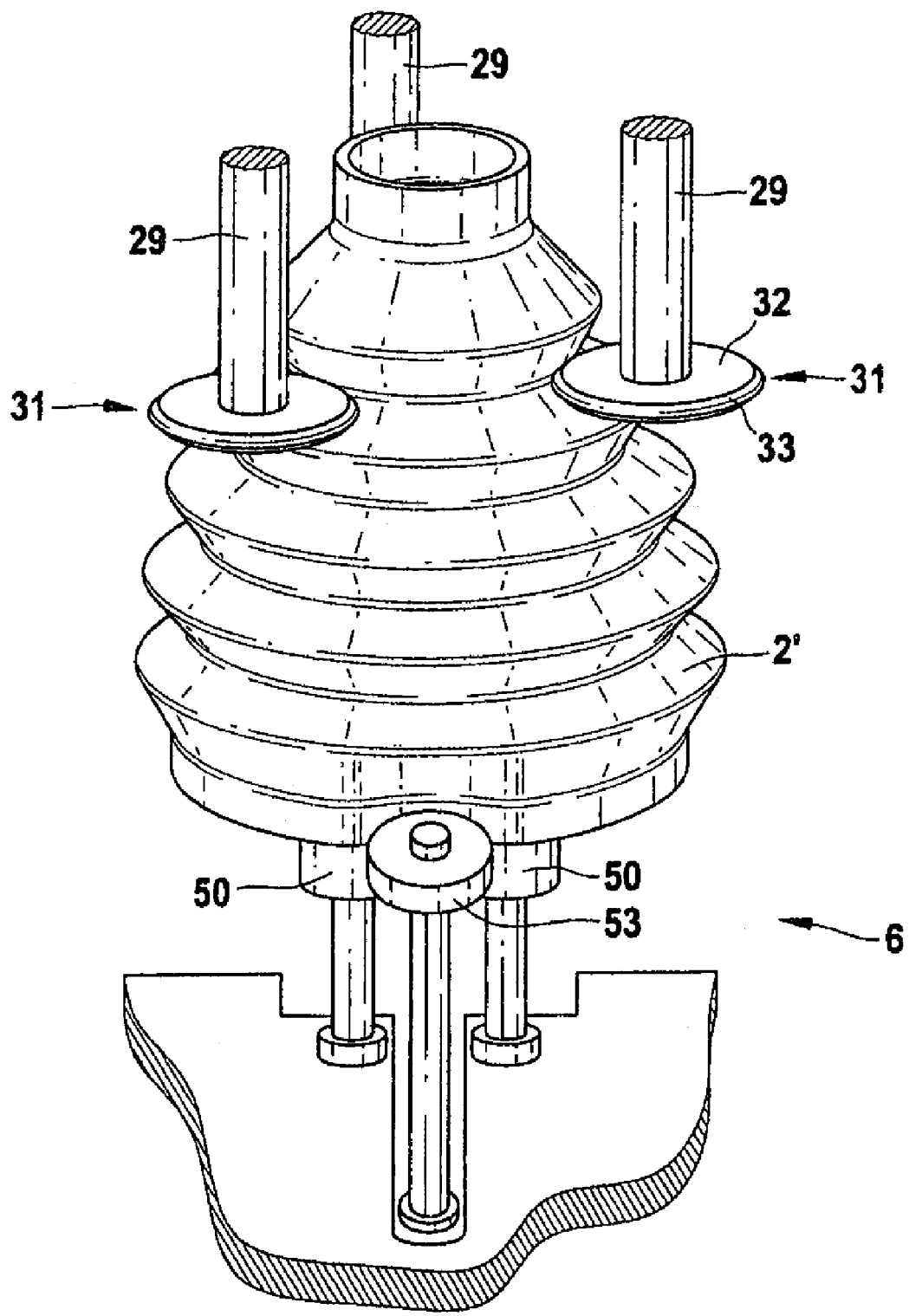
FIG. 7 shows the means shown in FIG. 5, with a deformed body held therein.

The body 2' illustrated in FIGS. 6 and 7 is an axle boot with a hollow-cylindrical shape and a cylinder casing in the form of bellows. The axle boot is made of a flexible material, in particular plastic or rubber.

The invention claimed is:

1. A gripper of a handling system for gripping a rotationally symmetrical body, wherein the gripper has gripping fingers with rotationally symmetrical holding elements for firmly holding the body, with the holding elements being mounted in the gripping fingers such that they can rotate about their rotation axes, and wherein the holding elements of the gripping fingers of the gripper are each connected in a rotationally fixed manner to a gearwheel, with the gearwheels of all the gripping finger of the gripper engaging indirectly via at least one further gearwheel with a central gearwheel of the gripper, and with the gripper having a first drive mechanism which causes the central gearwheel to carry out a rotational movement.

2. The gripper as claimed in claim 1, wherein the rotation axes of the holding elements run parallel to one another.

3. The gripper as claimed in claim 1, wherein the rotation axes of the holding elements run at right angles to the movement direction of the gripping fingers for gripping the body.

4. The gripper as claimed in claim 1, wherein the movement direction of the gripping fingers for gripping the body runs on a circular path.

5. The gripper as claimed in claim 1, characterized in wherein the first drive mechanism has an electric-motor drive.

6. The gripper as claimed in claim 1, wherein the gripping fingers of the gripper are connected in a rotationally fixed manner to a respective shaft, with the shafts running through the further gearwheels of the gripping fingers such that they can rotate, and with the gripper having a second drive mechanism which causes the shafts to carry out a rotary movement.

7. The gripper as claimed in claim 6, wherein the rotation axes of the shafts run parallel to the rotation axes of the gearwheels.

8. The gripper as claimed in claim 6, wherein the second drive mechanism has a pneumatic drive.

9. The gripper as claimed in claim 1 comprising means for optically scanning the rotationally symmetrical body during the rotational movement imparted by the central gearwheel.

10. The gripper as claimed in claim 9 further comprising means for deforming the rotationally symmetrical body during the rotational movement imparted by the central gearwheel and the optical scanning.

* * * * *